(12) United States Patent
Meyer et al.

(10) Patent No.: US 10,133,444 B2
(45) Date of Patent: Nov. 20, 2018

(54) PREFERRED VIEW GENERATION ON STRUCTURE LEVEL BASED ON USER PREFERENCES

(71) Applicant: KONINKLIJKE PHILIPS N.V., Eindhoven (NL)

(72) Inventors: Carsten Meyer, Hamburg (DE); Astrid Ruth Franz, Hamburg (DE); Thomas Heiko Stehle, Hamburg (DE); Fabian Wenzel, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/772,141

(22) PCT Filed: Mar. 18, 2014

(86) PCT No.: PCT/IB2014/059921
§ 371 (c)(1),
(2) Date: Sep. 2, 2015

(87) PCT Pub. No.: WO2014/155238
PCT Pub. Date: Oct. 2, 2014

(65) Prior Publication Data
US 2016/0004412 A1 Jan. 7, 2016

Related U.S. Application Data

(60) Provisional application No. 61/805,609, filed on Mar. 27, 2013.

(51) Int. Cl.
*G05G 5/00* (2006.01)
*G06F 3/0481* (2013.01)
(Continued)

(52) U.S. Cl.
CPC .......... *G06F 3/04817* (2013.01); *G06F 3/033* (2013.01); *G06F 3/0484* (2013.01);
(Continued)

(58) Field of Classification Search
None
See application file for complete search history.

(56) References Cited

U.S. PATENT DOCUMENTS 4,905,163 A 2/1990 Garber et al.
8,817,021 B1 * 8/2014 Hickman .......... G06F 17/30271
345/420

(Continued)

FOREIGN PATENT DOCUMENTS

WO 2008120155 A2 10/2008

*Primary Examiner* — Peter Hoang

(57) ABSTRACT

An apparatus and related method for image viewing. The apparatus (V) allows to store, learn and remember preferred user views $\alpha_{1-M}$ for each anatomical structure $F_1$-$F_N$ of interest. In any new image, the apparatus (V) affords automatically generating the preferred by the user for one or more of the structures ($F_1$-$F_N$) by a simple user input operation such as clicking with a mouse (PT) on any position within the displayed structure of interest ($F_1$-$F_N$).

15 Claims, 2 Drawing Sheets

(51) Int. Cl.
  *G06F 3/0484* (2013.01)
  *G06F 19/00* (2018.01)
  *G06F 3/033* (2013.01)
  *G06F 3/0489* (2013.01)
  *G06F 3/0485* (2013.01)

(52) U.S. Cl.
  CPC ........ *G06F 3/0489* (2013.01); *G06F 3/04842* (2013.01); *G06F 3/04845* (2013.01); *G06F 19/321* (2013.01); *G06F 3/0485* (2013.01)

(56) References Cited

U.S. PATENT DOCUMENTS

| | | |
|---|---|---|
| 9,069,575 B2 | 6/2015 | Mandyam et al. |
| 9,289,140 B2 | 3/2016 | Ross et al. |
| 2004/0109008 A1 | 6/2004 | Sako |
| 2008/0037850 A1 | 2/2008 | Assmann et al. |
| 2009/0002366 A1 | 1/2009 | Kanitsar et al. |
| 2009/0010520 A1 | 1/2009 | Wang |
| 2009/0067696 A1 | 3/2009 | Shinagawa et al. |
| 2009/0248996 A1* | 10/2009 | Mandyam ............ G06F 9/4443 711/154 |
| 2010/0100560 A1* | 4/2010 | Bystrov ................ G06F 19/321 707/769 |
| 2011/0087089 A1 | 4/2011 | Meinel et al. |

* cited by examiner

PREFERRED VIEW GENERATION ON STRUCTURE LEVEL BASED ON USER PREFERENCES

CROSS-REFERENCE TO PRIOR APPLICATIONS

This application is the U.S. National Phase application under 35 U.S.C. § 371 of International Application No. PCT/IB2014/059921, filed on Mar. 18, 2014, which claims the benefit of U.S. Provisional Application No. 61/805,609, filed on Mar. 27, 2013. These applications are hereby incorporated by reference herein.

FIELD OF THE INVENTION

The invention relates to an apparatus for image viewing, to a method for image viewing, to a computer program element, and to a computer readable medium.

BACKGROUND OF THE INVENTION

A good deal of work in certain professions is taken up by viewing imagery. In the medical profession, diagnostic work is oftentimes based on medical images such as X-ray projection images, magnetic resonance images, ultrasound images or images from other imaging modalities, as well as any combination thereof i.e. so-called multi-modality images. To visually inspect an anatomical structure of interest in an already acquired image, certain standard views are generated by an image processor or a viewing workstation that may prove not always optimal. Different viewing settings (e.g., different position, orientation, zooming etc) will need to be applied in order to optimize inspection of the structure of interest. Conversely, clinicians find it useful to apply similar viewing settings for corresponding images of different patients. Currently, however, the user has to manually generate similar viewing settings for each image. This can be tedious since it involves a number of steps, in particular input steps such as "mouse clicks", for each image. A conventional viewer is described in Applicant's US 2011/0087089.

SUMMARY OF THE INVENTION

There may therefore be a need for an apparatus to ease the burden on the user during image viewing tasks.

The object of the present invention is solved by the subject matter of the independent claims where further embodiments are incorporated in the dependent claims. It should be noted that the following described aspect of the invention equally apply to the method for viewing an image, to the computer program element and to the computer readable medium.

According to a first aspect of the invention there is provided an apparatus for image viewing, comprising: an input port for receiving a view request in form of a specification of an image region in a previously acquired image of an object, said image region representing a part of the object; a view preference retriever configured to return, in response to the request, a pre-stored view setting parameter associated with said object feature; a graphics display generator configured to generate a graphics display that, when displayed on a screen, affords to a human user a view on the object part as defined by the returned view setting parameter.

In other words as proposed herein the apparatus allows for an image feature guided image view parameter retrieval. In yet other words, rather than associating the view setting parameter with the actual image, the parameter is stored in association with a feature or part within the image. The feature, aspect, part or detail (hereinafter referred to in short as "feature") may be the pixel or voxel representation or an anatomical region of interest, such as a certain part of the human or animal brain. In other words, no matter the actual image in which the image region is specified, the same preferred view (as used in the previous viewing sessions) can be re-generated. It is sufficient for the currently displayed image to encode the region of interest in merely one arbitrary, initial view. Upon selection of that feature at the initial view, the apparatus then recovers, restores, or re-generates the user's preferred view for said feature. Using the pre-stored views per object feature, user preferred views can be exactly reproduced on demand.

Although the main application as envisaged herein is for medical images such as X-ray projections, 3D CT image volumes, magnetic resonance images and so forth, the apparatus can be likewise put to good use in other areas where professionals need to view or "review" large numbers of complex images, such as in geology or non-destructive material testing.

According to one embodiment, the view preference retriever operates to return said view setting parameter in dependence on a previous usage frequency of said view setting parameter for the object feature.

According to one embodiment, the viewer comprises a usage logger configured to update the previous usage frequency for an updated usage frequency thereby accounting for the occurrence of the request for the view parameter setting.

According to one embodiment, the returned view setting parameter is one of a plurality of pre-stored view setting parameters associated with i) the object feature and ii) a respective usage frequency, the returned view setting parameter's usage frequency being the highest from among the respective usage frequencies of the pre-stored view setting parameters or being higher than a pre-defined usage threshold.

According to one embodiment, the retriever operates to return said view setting parameter in response to a selection request by a user from a plurality of pre-stored view setting parameters associated with i) the object feature and ii) a respective usage frequency.

In one embodiment the user effects the selection by using a pointer tool such as computer mouse or stylus. In other embodiments, the selection is via a keyboard.

According to one embodiment, the selection request is issued by the user operating a pointer tool to select an interactive widget element from a plurality of widget elements of a graphical user interface displayed on the or a further screen, the plurality of widget elements representative of the plurality of pre-stored view setting parameters.

According to one embodiment, the selection request is issued by the user operating a pointer tool to select an interactive graphics widget from a plurality of interactive graphics widgets of a graphical user interface displayed on the or a further screen, each of the plurality of interactive graphics widgets forming a graphical representation of a view on the feature at the respective ones of the plurality of pre-stored view setting parameters.

According to one embodiment, the interactive widget elements or the interactive graphics widgets are displayed in a sorted manner according to the respective usage frequencies.

According to one embodiment, the view request is issued automatically upon loading the image for view into an image viewer. No user action for specifying the image portion is required thus increasing comfort and time efficiency. In one embodiment, the viewer automatically guesses which feature to the user is most likely to be interested in viewing. In this embodiment, the usage logger registers not only usage frequencies of the various view parameters but also usage frequencies of the various features, that is, the frequencies with which the respective features have been selected by the user for view, no matter the viewing parameter. In other words the logger tracks the number of times the particular feature is selected by the user or by the users in the group.

According to one embodiment, the graphics display generator is configured to receive, whilst the image is displayed on the screen at the returned view setting parameter, user instructions to change the view setting parameter into a new, not pre-stored, view setting parameter. This view parameter change effects the display on the screen of a new graphics display that affords a new view on the image/object feature. The usage logger is operable to capture the new view setting parameter as now in effect and to store the new view setting parameter in association with the object feature or in association with a newly selected object feature. The usage logger operates to maintain and update a usage frequency for the new viewing parameter when the retriever returns said new viewing parameter in response to a future request. The usage frequency is stored in association with the object feature or the newly selected object feature. In other words, the viewer apparatus as proposed herein operates to "learn" the viewing habits of the user (or a group of users) by counting user requests for the various settings.

According to one embodiment, the usage frequency measures i) a specific user's previous usage of the respective view setting parameter for that object feature or ii) a usage of the respective view setting parameter for that object by a group of users. In other words the knowledge of the group of users can be pooled thereby improving the learning capabilities of the viewer.

In sum, it is proposed herein to store, learn and remember preferred user views for each structure of interest. In any new image, the viewing system then automatically re-generates the current view preferred by the user for this structure merely by clicking with a pointer tool on any position within the structure. In embodiment is user input by mouse click action. A touch screen embodiment is also envisaged herein where stylus or finger touch action is used instead. In another embodiment user input for image feature selection is via keyboard though key combinations or user assignable "hot keys".

Definitions

"View" relates to how and which feature/part/detail/structure of a 2D image or a 3D image data volume or a 4D volume (time sequence of 3D volumes) is presented to the user on a screen. The term "view" is understood to relate to the inspection of an already acquired image, and not to settings to acquire an image.

"View settings/setting" is one or a collection of parameters that determine the view for any given image data when this image data is displayed on a screen/monitor/display unit.

"Rendering" is the generating of information suitable to control a video card of a computing system to drive the hardware of a screen/monitor/display unit to effect display thereon of a view of an image at a selected view setting.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
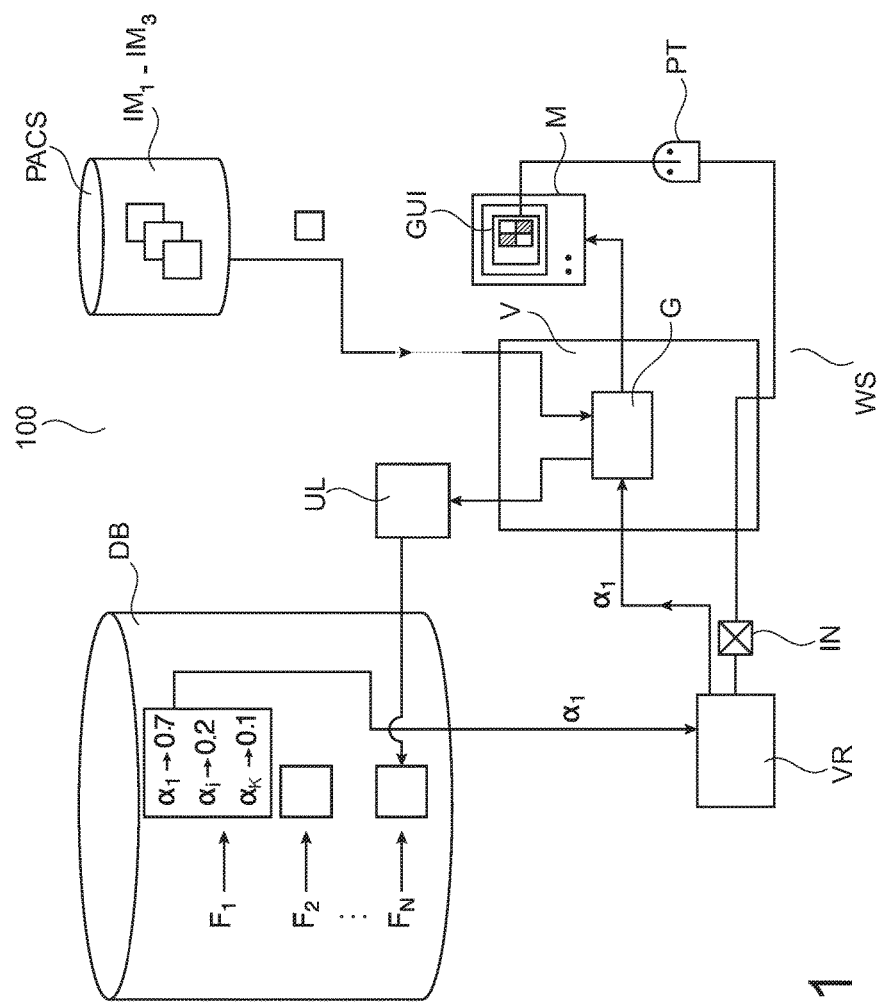
FIG. 1 shows a schematic block diagram of an image viewing arrangement.

With reference to FIG. 1 there is shown an arrangement 100 for aiding a clinician in visual inspection of medical imagery.

As its basic components said arrangement 100 includes a storage facility such as a PACS on which the imagery is held and a work station WS. Work station WS is essentially a computer unit communicatively coupled to said PACS for retrieval of said imagery.

The imagery referred to herein include digital images as acquired by an imaging modality or by a combination of different imaging modalities. For example images $IM_{1-3}$ include x-ray projection images or 3D image volumes acquired by CTs. Such imagery is held in the PACS in association with the respective patient ID, and further relevant information such as name, sex, age etc. An arbitrary image from the plurality of images $IM_{1-3}$ will simply be referred to hereinafter as "IM".

The arrangement further includes a monitor M for displaying the imagery and, as proposed herein, a new viewer module V. Among others and as will be explained in more details below, the viewer affords the user functionality to change a view setting parameter to control the visual manner in which the image is to be displayed.

Previously, a basic use scenario was as follows: the clinician ("user") invokes a conventional viewer. The viewer affords to the user several view manipulator functionalities. For instance a load button may allow the clinician to load a specific image of a specific patient into the viewer. The previous viewer then effects display on the screen M at default view. Typically the conventional viewer includes a "tool bar" or other graphical input means that allows the user to change in different combinations individual view setting parameters. View setting parameters include such settings as image position and orientation, zooming (factor) in and out, window/level setting, contrast levels, rotation of the field of view etc. For instance, the "image position" or "panning" parameter allows specifying which part of an image (or image volume) is to be viewed.

The window/level settings allows adapting the dynamic range of pixel intensities as recorded in the image to a smaller intensities range ("window") as recorded in a part of the image representative of an organ of interest. "Level" specifies the center of said window range. Other view parameters define the size of the rendered image on the screen M and where on the screen's plane the image is to be positioned. In "multi-pane" viewers, there is also a parameter for selecting the desired one of the panes where the rendered image is to be placed in.

Unlike the conventional viewer, it is proposed herein a new viewer V that eases the burden on the user when adjusting the view parameters which is normally a tedious process as the adjustment needs to be done for each image that is loaded. When similar viewing parameters are called for, the clinician, in previous systems, would have still had to adapt repeatedly to the desired view setting parameters for each image loaded into the viewer.

In the following the view setting parameter will be also designated as (view) parameter α. Parameter α may on occasion be thought of as a "scalar" value but will usually be more like a "vector" comprising a number of entries, one or more for each individual one of the previously described setting aspects (position, zoom, window/level, . . . ). Essentially, parameter α forms a collection of commands which are interpretable by a graphics display generator G. In other words, graphical display generator G forms the middle-ware (between the viewer V and the system's video card) for translating the commands into lower level signals to so eventually drive or control the individual pixels on the screen thereby effecting the display operation.

Briefly, and as will be explained in more detail below, the new image viewer V as proposed herein is operative to store, learn and remember preferred user view parameters for each anatomical structure of interest and to then automatically (re-)generate the view preferred by the individual clinician for this specific anatomic structure. Preferably operation of the arrangement is controlled by the user by a single input operation by a pointer tool PT (such as a mouse click) on the structure as displayed in the current image. As a main area of application it is envisaged to view previously acquired images.

More specifically, the arrangement operates in one embodiment to afford the functionality of storing one or more different viewing settings preferred by the user for each anatomical structure or for each landmark. The arrangement operates to maintain and automatically update prior probabilities (as approximated by usage frequencies of the respective viewing parameters) for the different views per structure, each time the user selects a particular view. In this manner the viewer operates to "learn" the preferred views. The arrangement allows to automatically re-generate the preferred user viewing setting in any new image based on a single user mouse click selection of any point making up the structure. In one embodiment the arrangement operates to offer alternative views (in a list or as thumbnail images) per structure based on the learned prior probabilities.

The image viewer V as proposed herein comprises as its main components a usage logger UL, a retriever VR (referred to herein as retriever) and an input port IN. Operation of the image viewer V apparatus will now be explained in more detail below with respect to the three modes of operation namely "storing/recording", "remembering/recalling", "learning" of view setting parameters α.

Operation

The image viewer V as proposed herein is essentially an event based module. The user uses the pointer tool PT (or, in some embodiments, a keyboard) to issue commands which are interpreted by the image viewer V in a context dependent manner.

The image viewer is operative to connect with a data base DB on which previously used view setting parameters $α_1, \ldots, α_i, \ldots, α_k$ are held. More specifically, and as shown diagrammatically in FIG. 1, each parameter $α_i$ is associated with a feature (anatomic structures) $F_i$ and a usage frequency.

Usage frequencies measures or approximates the probability that the user will use said parameter for a respective one of anatomic structures $F_i$. Usage frequencies, parameters α and structure IDs $F_i$ are held in an associative data structure. More specifically to each feature or anatomic structure F there is associated one or more parameters α and to each of those parameters there is associated the respective frequency with which the respective parameter was used for that associated structure. The associative structure facilitates look-up or retrieval operations. More specifically, in one embodiment, the array forms a "key-value" pair. Using the anatomic feature ID F as the "key", its associated "value" (that is, α and/or usage frequency) can be found. Associative data structures can be implemented in many computer languages such as "hashes" in Perl or "maps" in C or C++. Precisely how the usage frequencies are calculated in one embodiment, will be explained in more detail below with respect to the "learning" aspect of the viewer V's operation. Each of the anatomic feature identifiers (ID) $F_1$-$F_N$ identifies a specific anatomic structure in the human or animal body. In other words $F_1$-$F_N$, are strings denoting respective anatomic structures. In one embodiment, operation of viewer V is supported by segmentation. The feature IDs can then be matched against labels or annotations of image portions of the segmented image. In general, the result of the segmentation run is an annotated image. That is, the hitherto unstructured or uninterpreted pixel (or, as the case may be, voxel) information in the image is now structured into individual image portions, with each image portion (and hence each pixel within) being annotated with an ID $F_1$-$F_N$ of an anatomic structure that the respective image portion represents (that is, forms an image footprint of the relevant anatomic structure).

Storing/Recording Mode

The user invokes an instance of viewer V. The user then loads a certain image, say IM, into the viewer V by specifying patent ID, name or other metadata. Viewer V then connects to PACS and retrieves the specified image.

Viewer V then connects with the graphics display generator G. Graphics display generator G then operates, through a corresponding rendering operation and monitor M interfacing, to have said image IM displayed on monitor M at a default view in one embodiment or at an automatically established view as will be explained in more detail below.

The user then uses the viewer functionalities to manually adjust (the view parameters) as he sees fit in respect to a certain anatomic structure of interest. The image reviewer as proposed herein includes as a graphical user input means GUI which is displayed alongside the now current image IM on monitor M. The image reviewer GUI includes GUI dialogue windows with interactive control widgets ("button") and one or more message boxes. The message box invites the user to record or store the currently used view parameters. For instance, a text prompt may ask whether the user wishes to optimize the viewing setting for a particular structure of interest.

If the user decides to retain for future reference the currently used view parameter α, the user clicks on a "store/capture/record button" displayed on the image reviewer GUI. The viewer V then operates to capture all view settings that are necessary for a later re-generation of the now displayed view on the anatomy (or structure) of interest in image IM and consolidates the currently effective settings into parameter α. The image viewer V now listens for an event of the user designating a certain image portion representative of the anatomical structure with which the current view parameter is to be associated.

To facilitate this structure-to-a association operation, the previously mentioned segmenter is used to segment and interpret the current image at the current view. According to one embodiment, upon loading the image IM for view into the viewer, the segmenter automatically processes (in a background process) the image IM and "breaks" it up into different image portions each representative of a certain anatomic structure and annotates said image portions with an ID label as explained earlier. It is assumed herein that each of the anatomic structures so segmented are actually recognized, that is, can be matched to an identifier string or label. Should the segmentation process not terminate successfully, that is, if not all structures can be identified, an alert message is brought to the user's attention with the system highlighting the image portion whose segmentation was unsuccessful. The user can then decided on further steps, e.g., the user may wish to run a further segmentation based on a different algorithm. In one embodiment, the whole image is segmented. In a different embodiment, it is only the image portion around the user specified image point that is segmented, in other words, user specified image point is used as a segmentation seed point. Also, the segmentation can be initiated upon the user mouse-clicking into the image rather than initiating the segmentation of the whole image automatically upon loading the image into the viewer V.

Assuming the segmentation has been successful, the user issued click event of selecting a region of interest is intercepted by the image viewer V and the ID, say $F_3$, of the respective anatomic structure designated by said image portion is established in a look-up dictionary.

The image viewer then establishes contact with the data base DB and establishes by look-up operation in the associative array whether the now requested anatomical structure has been viewed in the past. If not, then a new associative data entry is adjoined to the existing data structure by using the ID of the new anatomic structure and the currently effective view parameter is stored in association with said ID. If however the ID matches a previous record, the newly used view parameter is stored in association with said pre-stored ID and adjoined to the existing entry.

The user may have more than one preference for a given structure. Therefore the viewer V supports recording multiple views per anatomic structure ID. Thus, after entering the recording or storing mode (that is upon actuation of the store button mentioned earlier), the user may record different preferred viewing settings per structure $F_3$. In one embodiment, the user is prompted by a dialogue message box to repeatedly adjust the view parameters to generate alternative views $\alpha_i$ for the same anatomic structure $F_3$. In this manner, the viewer V operates to record a list of preferred user view parameters $\alpha$ per anatomical structure $F_3$. If feature $F_i$ is also associated with its respective usage frequency (as will be explained in more detail below), a sorted list can be drawn up for the respective associative data structure entry $F_i$.

For each stored view $\alpha_i$, the user is prompted by a dialogue message box to enter a name for the viewing setting parameter $\alpha$, e.g. "hippocampus, coronal view enlarged". In one embodiment, default names VIEW1, VIEW2 with consecutive numbering are assigned as names if the user does not provide a name string. As mentioned, each of the views is associated with the given anatomical structure ID $F_3$, e.g., "hippocampus".

In one embodiment, rather than using user interaction via the pointer tool (or other input means) to initiate the association, the association between anatomical structure ID $F_3$ and the (possibly multiple) views $\alpha_i$ is effected instead manually by entering strings into a data form box.

Although in the above reference has been made to segmentation, in one embodiment a landmark localization algorithm is used instead and the views $\alpha_i$ are associated per landmark rather than per segmentation.

In one embodiment, alternatively or additionally to the above, the database DB is "pre-loaded" with a set of default/predefined views which are commonly used among many users to facilitate initial view generation.

Recall Mode

In this mode of operation it is again assumed that the user is viewing a current image at a selected or default view.

The user now specifies by mouse click PT a certain image portion representative of the anatomic structure of interest. This mouse click event is listened for by the image viewer V and is intercepted and forwarded to retriever RV. Retriever RV then translates the position of mouse click event into an ID, say $F_3$, by returning the label of the segment of which the pixel at the clicked-on position is part of. Operation of segmenter is again as explained earlier in the section "Storing Mode". Retriever VR then connects with the data base DB and uses the label of the segmented and clicked on anatomical structure to establish whether there are any views $\alpha_i$ available (that is, is pre-stored in the associative data structure) for this specific anatomic structure. If the retriever RV establishes no match, viewer V switches back into storage mode. In other words image viewer V operates to display a dialogue box on the screen M that invites the user to store a view parameter with the requested new anatomic structure.

If a match is found, the retriever RV returns the parameter $\alpha_i$ associated with said anatomical structure ID. If there is a plurality of views $\alpha_i$, the one having the highest usage frequency is returned. This most probable view parameter is then forwarded to the graphics display generator G which then operates to replace the currently used view parameter with the returned one and operates to affect the rendering of the image at the so returned view. In other words, the user when clicking on the respective anatomic structure has the impression that the system "remembers" the view the user has previously stored in the system for the clicked-on structure $F_3$. For instance, a mouse click on the hippocampus region in a brain MR image at a default view results in the associated view parameter being applied to the image. For instance, the image may be re-centered on the hippocampus region with a zooming-in action onto the hippocampus.

According to one embodiment, it is not necessarily the highest probability view that is returned but the one whose probability is higher than a certain user definable threshold. This allows saving CPU time because the system does not have to search for the highest probability view but is merely sufficient to find a view whose associated usage frequency is higher than the defined threshold.

To sum up, the operation in remember or recall mode, to automatically re-generate a preferred viewing setting a, for a given anatomical structure F in a new image, the user clicks on any position within the anatomical structure in the new image as displayed in a certain default view or user adjusted view. Based on automatic image segmentation, the system determines the anatomical structure corresponding to the position of the mouse click. Then, the system selects the stored view with the highest prior probability for the selected anatomical structure, i.e., applies the stored parameters to the image in order to generate the corresponding view.

All will be appreciated from the above, although the view parameter has been recorded based on a certain image or images, said view can be retrieved by retriever by clicking on the corresponding structure F in any image, even a completely new image not previously displayed. In this sense the viewer V as proposed herein allows "reviewing"

desired structures F across any image that is that encodes image information representative of said structure of interest.

In one embodiment, if there is a plurality of views $\alpha_i$ stored for the structure of interest, the names of the views for the anatomical structures are displayed to the user in form of a drop-down menu list. Alternatively, thumbnail images, one for each view are displayed, sorted according to their prior probabilities. The thumbnail images afford a miniature graphic representation of the currently viewed image at the respective views.

In an alternative embodiment, the views are not associated to anatomical structures identified by image segmentation, but to anatomical landmarks identified by an automatic landmark localization algorithm.

Learning Mode

The viewer V maintains and updates prior probabilities for the different user views $\alpha_i$. In particular, whenever the user selects one of the stored views for a given structure, the usage logger UL updates the prior usage frequency of this view parameter $\alpha$:

Let the prior probabilities of the k views stored by the system for any anatomical structure or landmark be $p_i = N_i/N$, where N denotes the total number of times a view has been returned for the anatomical structure, and $N_i$ denotes the number of times view i has been chosen for that structure, and $N_1 + N_2 + \ldots + N_k = N$. Then, if next time the user chooses view j, the prior probabilities are updated according to $$p_j = \frac{N_j + 1}{N + 1} \text{ and } p_i = \frac{N_i}{N + 1} \text{ for } i \neq j$$

This will increase the prior probability of the view that has just been selected to thereby "learn" the user's preference. Other mathematical implementations are likewise envisaged such as "smoothing" etc. In one embodiment weights are used to smooth the changes of the respective priors during updating. In this manner, (weight) updating is applied more conservatively, i.e., the effect of selecting views on the re-estimated prior probabilities is reduced or mitigated. The usage can be monitored for one specific user as identified when the user enters their credentials upon logging onto the work station. However, the user view preferences can also be "pooled" to thereby form a knowledge pool for preferred views for anatomic structures. In other words, in this embodiment, N (in the equation above) designates the aggregated total of usages of the respective view for the respective structure across all users of a group of qualified users (for example all physicians in a clinic). Whether or not a user is "qualified" can again be ascertained from their login credentials. For instance, only view parameters used by physicians will be accounted for by the usage logger UL. In this way, the professional knowledge as "enshrined" in the collection of usage frequencies accumulated during the day-to-day clinical practice across the group of physicians can be maintained and kept up to date.

According to one embodiment, when in recall or storing mode, the user selection of the image portion representative of the anatomic structure of interest is not effected by a mouse click but can also be implemented by keyboarded interaction. For example the user may press a key combination such as CTRL and the '+' or '−' key to cycle sequentially through each of the segmented anatomic structures with the currently selected anatomic structure highlighted in a different color for instance (or otherwise marked up).

According to yet another embodiment a touch screen implementation is used. Here, the selection of the respective image portions to request image viewing parameter is done by the user touching the respective image portion.

According to one embodiment the previously mentioned automatic segmentation into image portions may be executed before the image is evoked and loaded into the viewer V.

In yet another fully automatic embodiment, after the segmentation is completed, retriever RV connects with the data base DB and selects from among the stored image features the one that has the overall highest probability across all image features. In this manner the viewer V operates to ascertain from the segmented anatomic structures which one the user is likely to be interested in. The view with the highest probability associated with that high likelihood feature is then rendered for view and display. In this embodiment, there is no mouse-click required to effect the display of the most probable image feature at the most probable viewing parameter. Again, the user's login credentials may be evaluated. For instance, a neurologist of a special task unit for hippocampus research may be more likely to be interested in just that, the hippocampus region. In other words, in this embodiment the viewer V automatically guesses which feature to the user is most likely to be interested in viewing. In this embodiment, the usage logger UL registers not only usage frequencies of the various view parameters as explained above, but also usage frequencies of the various features, that is, the frequencies with which the respective features have been selected by the user for view, no matter the viewing parameter. In other words the logger UL tracks, using suitably arranged event counters, the number of times the particular feature is selected by the user or by the users in the group.

The components of the viewer V are envisaged to run as a module on the work station WS. The components may be programmed in a suitable scientific computing platform such as Matlab® or Simulink® and then translated into C++ or C routines maintained in a library and linked when called on by work station WS. However distributed architecture embodiment is also envisaged herein where the components are connected in a suitable communication network. The components may be arranged as dedicated FPGAs or as hardwired standalone chips. In one embodiment, viewer V runs centrally on a server and serves a number of work stations.

Although in the above embodiments, the data structure in database DB has been described with reference to an associative array, other implementations are likewise envisaged herein. For instance, the associations between the anatomic structures, the view parameters and the usage frequencies may be stored as linked/cross-referenced tables in a relational database system.

Figure 2:
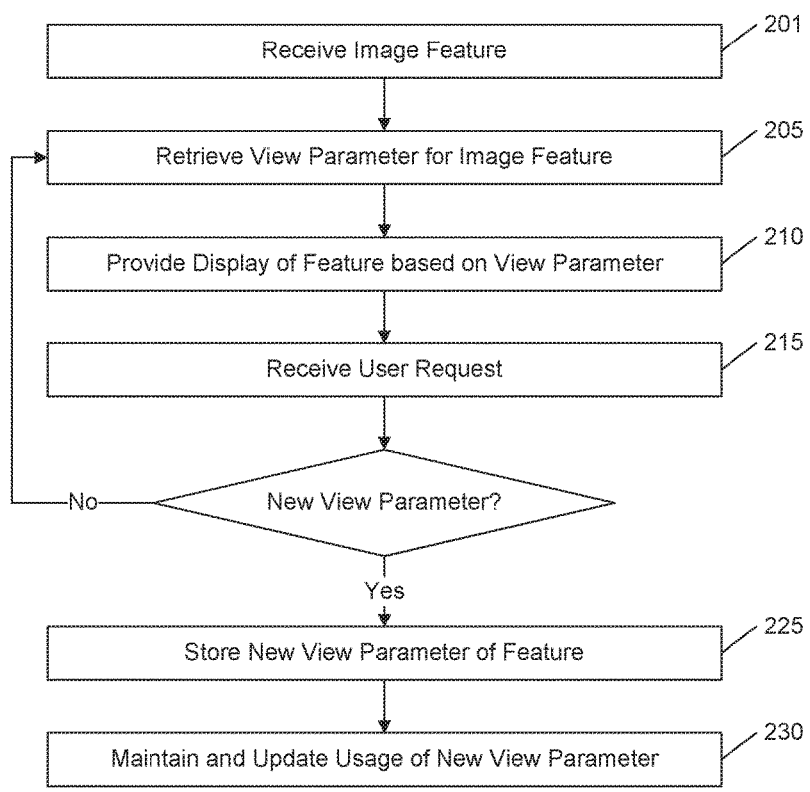
FIG. 2 is a flow chart for a method of image viewing.

With reference to FIG. 2 there is shown a flow chart of a method for viewing images.

At step S201 a view request in the form of a specification of an image region in a previously acquired image is received. The image portion represents a feature of an object, for example an anatomic region the user is interested in examining more carefully.

At step S205 a pre-stored view parameter $\alpha_i$ is retrieved which is associated with the image feature.

At step S210 a graphics display is generated and displayed on a screen. The so generated graphic display affords to the user a view on the object feature at the defined view parameter returned in the retrieving step S205.

At step S215 a user request is received to change for a different view setting parameter.

It is then determined at step S220 whether the requested, different view parameter is a new one, that is, whether the newly requested view setting parameter is already pre-stored in association with the object feature.

If the view parameter is not new, the view parameter is retrieved and the current view is updated for the requested view by using the newly retrieved view parameter.

If yes, that is, if the parameter is new, the user is asked in a dialogue component, for example a window widget bearing a message to this effect, whether the user wishes to store the newly requested view parameter for later reference with the object feature or with a new object feature.

If the user confirms, the new view parameter is captured and stored at step S225 in association with the selected object feature which may be the one previously shown or the newly selected one.

In one or more future steps (that is, after the association at step S225), whenever the user requests the newly associated view parameter for the respective object feature with which it has been previously stored/associated at step S225, said view parameter is retrieved and is used to render for view a new graphics display according to said view parameter. In response to the one or more future requests, the user's usage frequency for the now retrieved view parameter is updated at step S230 to so maintain and learn the user's behavior or view preference with respect to that object feature. It is understood this updating and counting operation to maintain usage frequencies is carried out for any pre-stored view parameter that is associated with a respective object feature.

The usage frequencies can be monitored by an event handler that listens for any view parameter request event issued by the user (or a group of users) and, specifically, for view request events in respect for any of those object features that are associated with the respective pre-stored view parameters. Each of these events, when picked up by the event handler, then increment a respective counter, that is, one for the total number of overall view requests and counters per object structure. Ratios can be computed from those counts to establish the respective usage frequencies which can serve as approximations of prior probabilities for the user requesting a respective view parameter for the respective object feature. In other words, the user frequencies measure, per object feature, the user's view preference or the view preference of the group of users.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for image viewing, comprising:
    a display device that displays an acquired image that comprises a plurality of features;
    an input circuit that receives a view request in form of a user selection of an image region in the display of the acquired image representing a select feature of the plurality of features in the acquired image; and a processor circuit that includes:
   a view settings retriever that returns from memory a plurality of sets of view setting parameters associated with the select feature, wherein each of the one or more sets of view setting parameters is independent of the acquired image and comprises at least: image positioning, image orientation, and image magnification; and
   a graphics display generator that generates a graphics display of a plurality of widget elements, each widget element providing an illustration of a view of the select feature using a respective set of view setting parameters of the plurality of view setting parameters;
wherein the input circuit receives a user selection of a preferred widget element; and
the graphics display generator generates a graphic display of a preferred view of the select feature using the respective set of view setting parameters associated with the preferred widget element.

2. The apparatus of claim 1, wherein the plurality of widget elements are displayed in a sorted manner according to respective usage frequencies of the sets of view setting parameters associated with the select feature.

3. The apparatus of claim 2, wherein the usage frequency measures i) a specific user's previous usage of the respective set of view setting parameters for the select feature or ii) a usage of the respective set of view setting parameters for the select feature by a group of users.

4. The apparatus of claim 2, wherein:
the processor circuit includes a usage logger that maintains and updates the usage frequency related to each of the sets of view setting parameters associated with the select feature each time the user selects the widget element associated with the respective set of view setting parameters.

5. The apparatus of claim 1, wherein:
the graphics display generator receives, whilst the preferred view is displayed on the screen, user instructions to change the respective set of view setting parameters into a new set of view setting parameters, thereby effecting the display on the screen of a new view of the select feature, and
the processor circuit adds the new set of view setting parameters to the plurality of sets of view setting parameters in memory.

6. A method of image viewing comprising:
displaying an acquired image that includes a plurality of features;
receiving a view request in form of a user selection of an image region in the acquired image, the image region representing a select feature of the plurality of features;
in response to the request, retrieving a plurality of sets of view setting parameters associated with the select feature from a memory circuit, wherein each of the sets of view setting parameters associated with the select feature is independent of the acquired image and comprises at least: image positioning, image orientation, and image magnification;
generating a graphics display of a plurality of widget elements, each widget element providing an illustration of a view of the select feature using a respective set of view setting parameters of the plurality of view setting parameters;
receiving a user selection of a preferred widget element; and
generating a graphic display of a preferred view of the select feature using the respective set of view setting parameters associated with the preferred widget element.

7. The method of claim 6, comprising:
receiving, whilst the preferred view is displayed on the screen, user instructions to change the respective set of view setting parameters into a new set of view setting parameters, thereby effecting the display on the screen of a new view of the select feature, and
adding the new set of view setting parameters to the plurality of sets of view setting parameters in memory.

8. The method of claim 6, comprising displaying the plurality of widget elements in a sorted manner according to respective usage frequencies of the sets of view setting parameters associated with the select feature.

9. The method of claim 8, wherein the usage frequency measures i) a specific user's previous usage of the respective set of view setting parameters for the select feature or ii) a usage of the respective set of view setting parameters for the select feature by a group of users.

10. The apparatus of claim 8, comprising maintaining and updating the usage frequency related to each of the sets of view setting parameters associated with the select feature each time the user selects the widget element associated with the respective set of view setting parameters.

11. A non-transitory computer-readable medium that includes a program that, when executed by a processing system, causes the processing system to:
display an acquired image on a screen, wherein the acquired image includes a plurality of features;
receive a view request in form of a user selection of an image region in the displayed acquired image, the image region representing a select feature of the plurality of features;
retrieve from memory a plurality of sets of view setting parameters associated with the select feature, wherein each of the sets of view setting parameters associated with the select feature is independent of the acquired image and comprises at least: image positioning, image orientation, and image magnification;
generate a graphics display comprising a plurality of widget elements, each widget element providing an illustration of a view of the select feature using a particular set of view setting parameters of the plurality of view setting parameters;
receive a user selection of a preferred widget element; and
generate a graphic display of a preferred view of the select feature using the particular set of view setting parameters associated with the preferred widget element.

12. The medium of claim 11, wherein the program causes the processing system to display the plurality of widget elements in a sorted manner according to respective usage frequencies of the sets of view setting parameters associated with the select feature.

13. The medium of claim 12, wherein the usage frequency measures i) a specific user's previous usage of the respective sets of view setting parameters associated with the select feature, or ii) a usage of the respective set of view setting parameters associated with the select feature.

14. The medium of claim 11, wherein the program causes the processing system to:
receive, whilst the preferred view of the select feature is displayed on the screen, user instructions to change the respective set of view setting parameters into a new set of view setting parameters, thereby effecting the display on the screen of a new view of the select feature, and store the new set of view setting parameters as an additional set of view setting parameters of the plurality of sets of view setting parameters associated with the select feature.

15. The medium of claim 12, wherein the program causes the processing system to update the usage frequency of the sets of view setting parameters associated with the select feature each time the user selects the associated widget element as the preferred widget element.

\* \* \* \* \*